US011033611B2

(12) United States Patent
Williams, III et al.

(10) Patent No.: US 11,033,611 B2
(45) Date of Patent: Jun. 15, 2021

(54) COMPOSITIONS AND METHODS FOR ADMINISTRATION OF AN ENZYME TO A SUBJECT'S AIRWAY

(71) Applicant: BOARD OF REGENTS, THE UNIVERSITY OF TEXAS SYSTEM, Austin, TX (US)

(72) Inventors: Robert O. Williams, III, Austin, TX (US); Steven Idell, Tyler, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/259,112

(22) Filed: Jan. 28, 2019

(65) Prior Publication Data

US 2019/0255157 A1    Aug. 22, 2019

Related U.S. Application Data

(62) Division of application No. 15/034,019, filed as application No. PCT/US2014/063784 on Nov. 4, 2014, now abandoned.

(60) Provisional application No. 61/899,739, filed on Nov. 4, 2013.

(51) Int. Cl.
*A61K 38/49*     (2006.01)
*A61K 9/00*      (2006.01)

(52) U.S. Cl.
CPC ............ *A61K 38/49* (2013.01); *A61K 9/0078* (2013.01); *A61K 9/008* (2013.01); *C12Y 304/21073* (2013.01)

(58) Field of Classification Search
CPC ...... A61K 38/49; A61K 9/0078; A61K 9/008; A61K 38/43; A61K 9/12; C12Y 304/21073; C12Y 304/21068; A61P 43/00; A61P 11/06; A61P 11/00
See application file for complete search history.

(56) References Cited

U.S. PATENT DOCUMENTS

| | | | |
|---|---|---|---|
| 4,790,305 A | 12/1988 | Zoltan et al. | |
| 5,302,390 A | 4/1994 | Browne et al. | |
| 5,531,219 A | 7/1996 | Rosenberg | |
| 2003/0113271 A1 | 6/2003 | Katyama et al. | |
| 2003/0219368 A1 | 11/2003 | Idell | |
| 2005/0036951 A1 | 2/2005 | Henderson | |
| 2005/0169908 A1 | 8/2005 | Murakami et al. | |
| 2006/0198940 A1 | 9/2006 | McMorrow | |
| 2007/0157931 A1 | 7/2007 | Parker | |
| 2007/0190183 A1* | 8/2007 | Green | A61K 2300/00 424/673 |
| 2010/0183620 A1 | 7/2010 | Bhawe et al. | |
| 2013/0039847 A1 | 2/2013 | Gessler et al. | |

FOREIGN PATENT DOCUMENTS

| | | |
|---|---|---|
| EP | 0266032 | 5/1988 |
| ES | 2 136 315 | 8/1997 |
| JP | 2014-529614 | 11/2014 |
| WO | WO 96/14056 | 5/1996 |
| WO | WO 98/06426 | 2/1998 |
| WO | WO 2010/034490 | 4/2010 |
| WO | WO 2013/029627 | 3/2013 |

OTHER PUBLICATIONS

Rüdiger et al., Journal of Critical Care, 2004, vol. 19, No. 1, p. 42-47.*
Dunn et al., Pharmaceutical Research, 2005, vol. 22, No. 10, p. 1700-1707.*
M.R. Wolfson, et al., "Understanding Airway Casts Secondary to Inhalational Smoke-induced Acute Lung Injury (ISALI); Independent Assessment Tools of Composition and Fibrinolysin Impact", ATS International Conference Abstract. Dated Oct. 31, 2018.
M.R. Wolfson, et al., "Perfluorochemical-Facilitated Fibrinolysin Delivery: Sustained Improvement in Physiologic Outcomes in Inhalational Smoke Induced Acute Lung Injury (ISALI) in Sheep", ATS International Conference Abstract. Dated Oct. 31, 2018.
Carr, Jason A., Karen J. Tietze, and Daniel L. Krinsky. "Asthmanefrin: Patient counseling opportunity." *Pharmacy Today* 19.11 (2013): 23.
Cheng Wan. Respiratory Medicine, vol. 1. Peking Union Medical College Press, 2007. pp. 121-123. Figures.
Higazi, Abd Al-Roof, et al. "Lysis of plasma clots by urokinase-soluble urokinase receptor complexes." *Blood* 92.6 (1998): 2075-2083.
International Preliminary Report on Patentability issued in International Application No. PCT/US14/63784, dated May 19, 2016.
International Search Report and Written Opinion issued in International Application No. PCT/US14/63784, dated Mar. 13, 2015.
Johnson, Jeremy C., et al. "Aerosol delivery of recombinant human DNase I: in vitro comparison of a vibrating-mesh nebulizer with a jet nebulizer." *Respiraiory Care* 53.12 (2008): 1703-1708.
Laterre, Pierre-François, Xavier Wittebole, and Jean-François Dhainaut. "Anticoagulant therapy in acute lung injury." *Critical Care Medicine* 31.4 (2003): S329-S336.
Münster, A-MB, et al. "Effects of inhaled plasminogen activator on the balance between coagulation and fibrinolysis in traumatized pigs." *Blood Coagulation & Fibrinolysis* 13.7 (2002): 591-601.
Müster, et al. "Jet and ultrasonic nebulization of single chain urokinase plasminogen activator (scu-PA)." *Journal of Aerosol Medicine* 13.4 (2000): 325-333.
Newbrough, J., "Just Nebulizers blog", Mar. 2012, 1 page.
Office Communication Issued in Chinese Application No. 201480060878.2, dated May 2, 2018. (English Translation).
Office Communication issued in Colombian Application No. 16-128.893, dated Dec. 27, 2017. (English Translation).
Office Communication issued in Colombian Application No. 16-128.893, dated Jul. 5, 2018. (English Translation).

(Continued)

*Primary Examiner* — Kade Ariani
(74) *Attorney, Agent, or Firm* — Parker Highlander PLLC

(57) ABSTRACT

Methods and composition for delivery of enzymes to a subject's airway. In some aspects, nebulized composition of enzymes, such as plasminogen activators are provided. In further aspects perfluorocarbon compositions comprising enzymes, such as plasminogen activators are provided. Compositions may, in some aspects, be used for the treatment of lung infections or acute lung injury, such as inhalational smoke induced acute lung injury (ISALI).

15 Claims, 3 Drawing Sheets

(56) References Cited

OTHER PUBLICATIONS

Office Communication Issued in U.S. Appl. No. 15/034,019, dated Jan. 3, 2018.
Office Communication issued in U.S. Appl. No. 15/034,019, dated Sep. 27, 2018.
Partial Supplementary Search Report issued in European Application No. 14857307.4, dated May 15, 2017.

* cited by examiner

COMPOSITIONS AND METHODS FOR ADMINISTRATION OF AN ENZYME TO A SUBJECT'S AIRWAY

This application is a divisional of U.S. patent application Ser. No. 15/034,019, filed May 3, 2016, as a national phase application under 35 U.S.C. § 371 of International Application No. PCT/US2014/063784, filed Nov. 4, 2014, which claims the benefit of U.S. Provisional Patent Application No. 61/899,739, filed Nov. 4, 2013, the entirety of which are incorporated herein by reference.

This invention was made with government support under Grant no. P01 HL076406 and R01 HL118401 awarded by the National Institutes of Health. The government has certain rights in the invention.

BACKGROUND OF THE INVENTION

1. Field of the Invention

The present invention relates generally to the field of molecular biology, drug delivery and medicine. More particularly, it concerns compositions and methods for the delivery of therapeutic enzyme compositions to a subject's respiratory system.

2. Description of Related Art

Many patients with severe burns and smoke exposure develop a severe form of ALI (Acute Lung Injury) called the Acute Respiratory Distress Syndrome (ARDS) that is associated with a mortality of 30-40%, protracted hospitalization and long-term morbidity. Inhalational smoke (IS)-induced ALI (ISALI) is characterized by severe airway obstruction, fibrinous airway casts or debris and alveolar fibrin deposition. Effective, specific treatment for ISALI is now lacking.

Burn injuries affect over 1 million patients in the United States annually and ISALI affects thousands of smoke-exposed patients in civilian and military practice annually (Enkhbaatar et al., 2004a). ISALI contributes to more than 3000 deaths and 17,000 fire-related injuries in the United States annually and a fire-related mortality rate of 2-3/100,000 population, which is one of the highest in the developed world [Committee on injury and poison prevention (2000) Pediatrics 105:1355-1357]. Supportive care is suboptimal, protracted and expensive. Outcomes entail significant mortality and morbidity. Despite current supportive care including mechanical ventilation, the mortality rate of ARDS, including that associated with ISALI, approaches 30-40 percent (Phua et al., 2009).

These considerations demand the testing of new and potentially more effective therapy. ISALI is associated with severe respiratory impairment, protracted hospitalization and, often, the requirement for mechanical ventilation. Long-term complications of ISALI include bronchial reactivity, accelerated pulmonary fibrosis and bronchiectasis. Among all forms of ALI, ISALI is especially prone to aberrant fibrin turnover including fibrin casts that form in the large airways and fibrin in the alveoli (Enkhbaatar et al., 2004a). Bronchial casts interfere with gas exchange, often require bronchoscopic clearance and promote atelectasis. While nebulized heparin and N-acetylcycteine are used in clinical practice, the efficacy of nebulized heparin in patients with ISALI remains unproven in any randomized or prospectively controlled clinical trials (Tuinman et al., 2012), nor has heparin alone been shown to improve ISALI when tested in our studies in sheep (Enkhbaatar et al., 2008a; Enkhbaatar et al., 2008b). Heparin does not clear established clots and nebulized heparin can initiate systemic coagulopathy in ISALI (O'Donnell, 2012)

SUMMARY OF THE INVENTION

Provided herein is method of preparing an enzyme solution for administration to a subject's airway that includes nebulizing the enzyme solution (e.g., using a vibrating mesh nebulizer). The enzyme can be a tissue plasminogen activator, which includes a single chain urokinase plasminogen activator (scuPA) and a tissue plasminogen activator (tPA). In some embodiments, the vibrating mesh nebulizer is an AERONEB® Professional Nebulizer or an EZ Breathe Atomizer.

Thus, in a first embodiment there is provided a method of preparing an enzyme solution for administration to a subject's airway comprising nebulizing the enzyme solution to provide a nebulized solution. In certain aspects, the enzyme may be a plasminogen activator, such as a single chain urokinase plasminogen activator (scuPA) or a tissue plasminogen activator (tPA). In certain aspects, nebulizing the enzyme solution may be by using a vibrating mesh nebulizer. In some aspects, nebulizing the enzyme solution does not comprise use of a jet nebulizer or an ultrasonic nebulizer. In certain aspects, nebulizing an enzyme solution of the embodiments may comprise providing sufficient nebulization energy and/or time to provide a nebulized solution having a median droplet size of between about 2.5 µm and 10 µm, 2.5 µm and 8 µm, or 3.0 µm and 6 µm. In some specific aspects, nebulizing the enzyme solution comprises obtaining a lyophilized enzyme composition, reconstituting the lyophilized enzyme composition in a solution (e.g., an aqueous solution) to provide an enzyme solution, and nebulizing the enzyme solution. Thus, in a further embodiment, there is provided a nebulized enzyme solution produced in accordance with the methods of the embodiments.

In still a further embodiment, there is provided a composition comprising a nebulized solution of scuPA or tPA. In some aspects, composition or enzyme solution of the embodiments may be an aqueous solution. In certain aspects, the enzyme solution comprises a physiologically acceptable salt concentration and/or a pH buffering agent. For example, enzyme solution may be a sterile saline solution or phosphate buffered saline (PBS). In preferred aspects, the composition or enzyme solution comprises scuPA.

In a further embodiment, a method treating a subject is provided comprising administering a nebulized enzyme solution (e.g., a tPA and/or scuPA enzyme solution) to the airway of a subject in need thereof. For example, the subject may have an acute lung injury or infection. In still further aspects, subject for treatment has inhalational smoke induced acute lung injury (ISALI), chemical-induced lung injury, plastic bronchitis, severe asthma, or acute respiratory distress syndrome (ARDS). In this embodiment, the plasminogen activator is nebulized using nebulizer, such as a vibrating mesh nebulizer (e.g., the AERONEB® Professional Nebulizer or the EZ Breathe Atomizer). The skilled artisan understands that any type of atomizer, such as a nebulizer, that delivers a therapeutically and pharmaceutically acceptable dose of the enzyme is suitable for use according to the embodiments.

In a further embodiment, there is provided a composition comprising a plasminogen activator and a perfluorocarbon (e.g., a "breathing liquid"). In some aspects, the plasminogen activator is scuPA and/or tPA. In some aspects, the perfluorocarbon may comprise a cycloalkyl group. For example, the perfluorocarbon may be perfluorodecalin and/or perfluoro-octylbromide.

Another further embodiment of the invention provides a method for treating a subject having a lung infection or lung injury comprising administering to the subject a therapeutically effective amount of a composition comprising a plasminogen activator and a perfluorocarbon. In some aspects, the plasminogen activator is a scuPA or a tPA. In certain aspects, the perfluorocarbon may be perfluorodecalin and/or perfluoro-octylbromide.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figures 3, 4:
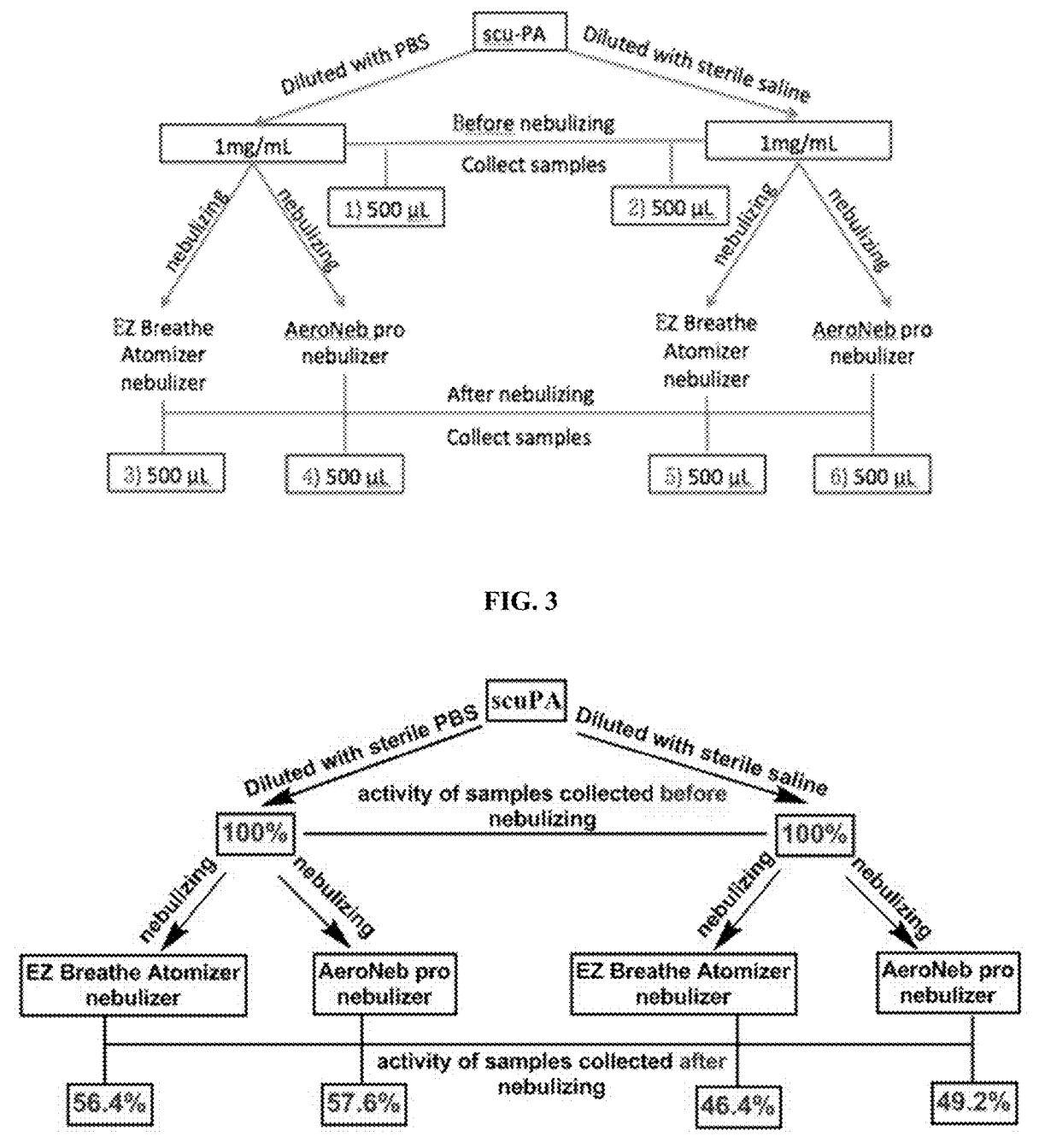

FIG. 3 is a schematic showing the methods of preparing several different nebulized single chain urokinase plasminogen activator (scuPA) formulations.

FIG. 4 is a schematic showing the activity of the nebulized scuPA formulations prepared according to FIG. 3.

FIG. 5 is a schematic showing the activity of tissue plasminogen activator (tPA) once mixed with perfluorodecalin (PFD) or perfluoro-octylbromide (PFB).

DESCRIPTION OF ILLUSTRATIVE EMBODIMENTS

I. The Present Invention

Provided herein is a method of preparing an enzyme solution for administration to a subject's airway comprising nebulizing the enzyme solution using a nebulizer, such as a vibrating mesh nebulizer. It is a surprising finding of the present studies detailed herein that nebulization of enzymes, such by using a vibrating mesh nebulizer, results in nebulized compositions that maintain significant enzymatic activity levels. Also provided herein is a method of treating lung injuries and infections, such as inhalational smoke induced acute lung injury (ISALI) in a subject by administering to the subject a therapeutically effective amount of a nebulized plasminogen activator via an airway. In some cases, the plasminogen activator is nebulized using a vibrating mesh nebulizer. Further provided herein is a composition comprising a plasminogen activator and a perfluorocarbon, and a method for using the plasminogen activator/perfluorocarbon composition to treat lung injury and infection (e.g., ISALI). In some embodiments, an enzyme for use according to the embodiments is a proenzyme. In further aspects, the enzyme a plasminogen activator.

In still further embodiments, an enzyme for use herein is a plasminogen activator selected from tPA and scuPA. The terms "tissue plasminogen activator" and "tPA" are used interchangeably and refer herein to a serine protease (in some embodiments, EC 3.4.21.68) that can be involved in the conversion of plasminogen to plasmin. It should be understood that the terms "tissue plasminogen activator" and "tPA" include recombinant forms including, but not limited to, altepase, reteplase, tenecteplase, and desmoteplase. The terms "tissue plasminogen activator" and "tPA" further include the single chain form (sc-tPA), the two chain form (ds-tPA), and mixtures thereof. In some embodiments, the tPA is a human tPA or a human-derived tPA. The terms "single chain urokinase plasminogen activator" and "scuPA" are used interchangeably and refer herein to a proenzyme of a urokinase serine protease (in some embodiments, EC 3.4.21.73), which serine protease can be involved in the conversion of plasminogen to plasmin. The "single chain urokinase plasminogen activator" or "scuPA" can be activated by proteolytic cleavage between Lys158 and Ile159, resulting in two chains linked by a disulfide bond that form the serine protease enzyme. Example 3 and FIG. 4 below describe the nebulization of scuPA using a vibrating mesh nebulizer and the surprisingly high enzymatic activity achieved following nebulization as compared to prior art methods of nebulization. In some embodiments, the vibrating mesh nebulizer is an AERONEB® Professional Nebulizer or an EZ Breathe Atomizer.

The term "enzyme solution" refers herein to any liquid formulation containing an enzyme that is suitable for nebulization. In some embodiments, the enzyme solution contains a pharmaceutically acceptable carrier or excipient as defined herein. The enzyme solution is administered to a subject's airway via inhalation or any other method known to those of skill in the art. The term "airway" refers herein to any portion of the respiratory tract including the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

Also provided herein is a method of treating inhalational smoke induced acute lung injury (ISALI) in a subject comprising administering to the subject a therapeutically effective amount of a nebulized plasminogen activator via an airway, wherein the plasminogen activator is nebulized using a vibrating mesh nebulizer. In some embodiments, the plasminogen activator is selected from a tPA and a scuPA. In other or further embodiments, the vibrating mesh nebulizer is an AERONEB® Professional Nebulizer or an EZ Breathe Atomizer.

It should be understood that "treating ISALI" indicates partially or completely delaying, alleviating, mitigating or reducing the intensity of one or more attendant symptoms of a disorder or condition such as an ISALI condition and/or alleviating, mitigating or impeding one or more causes of a disorder or condition such as an ISALI condition. Treatments according to the invention may be applied preventively, prophylactically, pallatively or remedially. In some instances, the terms "treat," "treating," "treatment" and grammatical variations thereof include partially or completely reducing a condition or symptom associated with an ISALI condition as compared with prior to treatment of the subject or as compared with the incidence of such condition or symptom in a general or study population. In some embodiments, an ISALI condition includes one or more of: reduced oxygenation, airway obstruction (including a severe airway obstruction), fibrinous airway casts or debris, and alveolar fibrin deposition. Accordingly, treating an ISALI condition includes one or more of improvement of oxygenation, reduced airway obstruction, reduced fibrinous airway casts or debris, and reduced alveolar fibrin deposition. In some embodiments, an ISALI condition is treated with a reduced incidence of bleeding.

Further provided herein is a composition comprising a plasminogen activator and a perfluorocarbon (PFC). In some embodiments, the plasminogen activator in the composition is selected from a tPA and a scuPA. In other or further embodiments, the PFC in the composition is selected from perfluorodecalin, perfluoro-1,3-dimethylcyclohexane, FC-75, perfluorooctane and perfluoro-octylbromide. In some aspects, PFC is or comprises a PFC having a cycloalkyl group, such as perfluorodecalin, perfluoro-1,3-dimethylcyclohexane or FC-75. It should be understood that the plasminogen activator and PFC can be in any ratio or concentration. In some embodiments, the composition comprises a plasminogen activator at a concentration of approximately 0.005-0.040 mg/mL of PFC.

Figure 5:
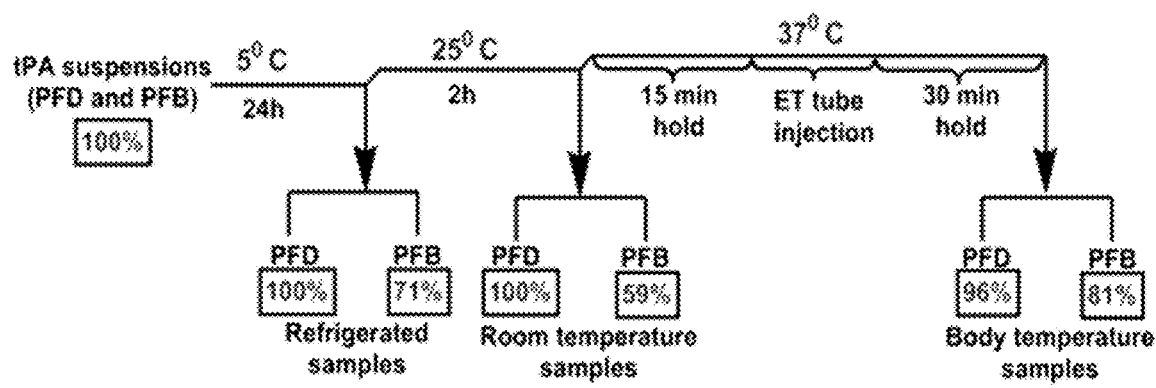

Still further provided is a method of treating inhalational smoke induced acute lung injury (ISALI) in a subject comprising administering to the subject a therapeutically effective amount of a composition comprising a plasminogen activator and a PFC. Example 4 and FIG. 5 demonstrate that a plasminogen activator, tPA, retained activity in a perfluorocarbon mixture. Further, the PFC and plasminogen activator additively foster airway debris removal as well as clearance of alveolar fibrin and improved outcome. Specifically, the PFC effectively delivers the plasminogen activator which promotes 1) dissolution and dislodgement of the airway casts; and 2) removal of airway and alveolar debris while supporting respiratory gas exchange. Mechanistically, the PFC effectively recruits lung volume. Given the low surface tension of the PFC liquid, the PFC distributes the plasminogen activator throughout the lung, potentially between casts and airway wall, thus breaking down the casts as they are being formed while slowing formation of new casts. As the PFC volatizes from the lung, the plasminogen activator remains to further act to dissolve airway casts and alveolar fibrin. Upon redosing with PFC suspensions, the PFC volumes not only deposit additional drug but dislodge the casts and alveolar debris. Because the PFC is incompressible, it stents open damaged small airways and thereby aids recruitment. Although we are not bound by any certain mechanism, contact with PFCs may also protect the underlying epithelium through attenuation of coagulation, which is initiated by tissue factor in the small airways and alveoli in virtually all forms of ALI. With in-line suctioning, the lower density debris float in the relatively more dense PFC, facilitating removal of airway fibrin cast fragments and debris.

Accordingly, in some embodiments of the method of administering a plasminogen activator and PFC composition, the plasminogen activator is selected from a tPA and a scuPA. In other or further embodiments of the method of administering a plasminogen activator and PFC composition, the PFC in the composition is selected from perfluorodecalin and perfluoro-octylbromide.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes. Term definitions used in the specification and claims are as follows.

II. Definitions

As used in the specification and claims, the singular form "a," "an," and "the" include plural references unless the context clearly dictates otherwise. For example, the term "a cell" includes a plurality of cells, including mixtures thereof.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques. In some embodiments, the administration is via inhalation of a nebulized composition.

The term "airway" refers herein to any portion of the respiratory tract including the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

A "composition" is intended to mean a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." "Mammal" for purposes of treatment refers to any animal classified as a mammal, including a human, domestic and farm animals, nonhuman primates, and zoo, sports, or pet animals, such as dogs, horses, cats, cows, etc.

The term "enzyme" refers herein to one or more polypeptides that catalyze a specific biochemical reaction or to a proenzyme. The term "proenzyme" refers to a biologically active substance that is metabolized into an enzyme. In one embodiment, the enzyme is a tissue plasminogen activator (tPA). In other or further embodiments, the enzyme is a proenzyme and is a single chain urokinase plasminogen activator (scuPA).

The term "fibrinolysin" refers herein to any of several proteolytic enzymes that promote the dissolution of blood clots. A fibrinolysin includes, but is not limited to, plasmin, tissue plasminogen activator (tPA, sc-tPA and dc-tPA), urokinase (uPA), and urokinase proenzymes (scuPA).

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The terms "inhalational smoke induced acute lung injury" and "ISALI" are used interchangeably herein and refer to a form of acute lung injury (ALI) caused by smoke inhalation. ALI is also referred to as "mild ARDS." ALI can be defined by finding one or more of the following conditions in a subject: 1) bilateral pulmonary infiltrates on chest x-ray, 2) when measured by right heart catheterization as clinically indicated, pulmonary capillary wedge pressure <18 mmHg (2.4 kPa), and 3) PaO2/FiO2<300 mmHg (40 kPa). In some embodiments, treatment of ISALI includes treatment of one or more of the following conditions: reduced oxygenation, airway obstruction (including a severe airway obstruction), fibrinous airway casts or debris, and alveolar fibrin deposition.

The terms "nebulizing," "nebulized" and other grammatical variations, refer herein to the process of converting a liquid into small aerosol droplets. In some embodiments, the aerosol droplets have a median diameter of approximately 2-10 μm. In some embodiments, the aerosol droplets have a median diameter of approximately 2-4 μm.

The terms "perfluorocarbon" and "PFC" are used interchangeably and refer herein to an organofluorine compound that contains predominantly carbon and fluorine. It should be understood that the term "perfluorocarbon" is meant to include highly fluorinated molecules that contain molecules in addition to carbon and fluorine, and are commonly referred to as fluorocarbons. Examples of perfluorocarbons include, but are not limited to, perfluorodecalin, perfluorooctylbromide, FC 77, PF 5060 and Rimar 101. PFCs used according to the present invention share similar physicochemical properties with respect to gas solubility, density and surface tension but may differ with respect to radioopacity and kinematic viscosity which could have an impact on visualization and mobility of airway casts during debridement. Each listed perfluorocarbon includes all relevant isomers such as stereoisomers, enantiomers, and diastereomers.

The term "plasminogen activator" refers to a serine protease polypeptide that conversts plasminogen to plasmin, and includes, but is not limited to, tPA, uPA (two chain or active forms) and a proenzyme scuPA as defined herein.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" or "excipient" encompasses any of the standard pharmaceutical carriers, such as a phosphate buffered saline solution, saline (including sterile saline), water, and emulsions, such as an oil/water or water/oil emulsion, where "oil" represents the water immiscible phase of the emulsion that is pharmaceutically acceptable, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The term "pharmaceutically acceptable salts" refers to any acid or base addition salt whose counter-ions are non-toxic to the subject to which they are administered in pharmaceutical doses of the salts. Specific examples of pharmaceutically acceptable salts are known to those of ordinary skill in the art.

The terms "pharmaceutically effective amount," "therapeutically effective amount," or "therapeutically effective dose" refer to the amount of a compound such as an ACPD composition that will elicit the biological or medical response of a tissue, system, animal, or human that is being sought by the researcher, veterinarian, medical doctor or other clinician.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE;

Databases=non-redundant, GenBank+EMBL+DDBJ+PDB+GenBank CDS translations+SwissProtein+SPupdate+PIR.

The terms "prevent," "preventing," "prevention," and grammatical variations thereof as used herein refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "pharmaceutically effective amount," "therapeutically effective amount," or "therapeutically effective dose" refer to the amount of a compound such as a tPA and/or scuPA composition that will elicit the biological or medical response of a tissue, system, animal, or human that is being sought by the researcher, veterinarian, medical doctor or other clinician.

The terms "single chain urokinase plasminogen activator" and "scuPA" are used interchangeably and refer herein to a proenzyme of a urokinase serine protease polypeptide (in some embodiments, EC 3.4.21.73), which serine protease can be involved in the conversion of plasminogen to plasmin, or to a proenzyme as described in U.S. Pat. No. 7,332,469, incorporated herein by reference. The "single chain urokinase plasminogen activator" or "scuPA" can be activated by proteolytic cleavage between Lys158 and Ile159, resulting in two chains linked by a disulfide bond that form the serine protease enzyme. It should be understood that scuPA homologs are also included in the present invention. The term "scuPA homolog" refers herein to homologs, orthologs, and paralogs of the proenzyme of the urokinase serine protease polypeptide identified as EC 3.4.21.73 and other sequences having greater than 70% homology to the proenzyme of the urokinase serine protease polypeptide identified as EC 3.4.21.73, or to a proenzyme as described in U.S. Pat. No. 7,332,469.

A "subject," "individual" or "patient" is used interchangeably herein, which refers to a vertebrate, preferably a mammal, more preferably a human. Mammals include, but are not limited to, murines, simians, humans, farm animals, sport animals, and pets.

The term "therapeutically effective amount" includes that amount of a compound such as a tPA and/or scuPA composition that, when administered, is sufficient to prevent development of, or alleviate to some extent, one or more of the symptoms of an ISALI abnormality being treated. The therapeutically effective amount will vary depending on the compound such as a tPA and/or scuPA composition, the disorder or conditions and their severity, the route of administration, the time of administration, the rate of excretion, the drug combination, the judgment of the treating physician, the dosage form, and the age, weight, general health, sex and/or diet of the subject to be treated.

The terms "tissue plasminogen activator" and "tPA" are used interchangeably and refer herein to a serine protease (in some embodiments, EC 3.4.21.68) that can be involved in the conversion of plasminogen to plasmin. It should be understood that the terms "tissue plasminogen activator" and "tPA" include recombinant forms including, but not limited to, altepase, reteplase, tenecteplase, and desmoteplase. The terms "tissue plasminogen activator" and "tPA" further include the single chain form (sc-tPA), the two chain form (ds-tPA), and mixtures thereof. In some embodiments, the tPA is a human tPA or a human-derived tPA. It should also be understood that tPA homologs are also included in the present invention. The term "tPA homolog" refers to homologs, orthologs, and paralogs of the tissue plasminogen activator polypeptide identified as EC 3.4.21.68 and other sequences having greater than 70% homology to the tissue plasminogen activator polypeptide identified as EC 3.4.21.68. In some embodiments, the tPA is a single chain form such as the ALTEPASE™ form.

The terms "treat," "treating," "treatment" and grammatical variations thereof as used herein include partially or completely delaying, alleviating, mitigating or reducing the intensity of one or more attendant symptoms of a disorder or condition such as an ISALI condition and/or alleviating, mitigating or impeding one or more causes of a disorder or condition such as an ISALI condition. Treatments according to the invention may be applied preventively, prophylactically, palliatively or remedially. In some instances, the terms "treat," "treating," "treatment" and grammatical variations thereof include partially or completely reducing a condition or symptom associated with an ISALI condition as compared with prior to treatment of the subject or as compared with the incidence of such condition or symptom in a general or study population. In some embodiments, an ISALI condition includes one or more of: reduced oxygenation, airway obstruction (including a severe airway obstruction), fibrinous airway casts or debris, and alveolar fibrin deposition. In some embodiments, an ISALI condition is treated with a reduced incidence of bleeding.

The term "vibrating mesh nebulizer" refers herein to any nebulizer that operates on the general principle of using a vibrating mesh or plate with multiple aperatures (an aperture plate) to generate a fine-particle, low-velocity aerosol. Some nebulizers may contain a mesh/membrane with between 1000 and 7000 holes, which mesh/membrane vibrates at the top of a liquid reservoir (see, e.g., U.S. Patent Publn. 20090134235 and Waldrep and Dhand 2008, each incorporated herein by reference). In some embodiments, the vibrating mesh nebulizer is an AERONEB® Professional Nebulizer, Omron MICROAIR®, Pari EFLOW® or an EZ Breathe Atomizer. In some aspects, a vibrating mesh nebulizer has a vibrating frequency of between about 50-250 kHz, 75-200 kHz 100-150 kHz or about 120 kHz. These devices have a high efficiency of delivering aerosol to the lung and the volume of liquid remaining in these devices is minimal, which is an advantage for expensive and potent compounds like plasminogen activators.

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1:
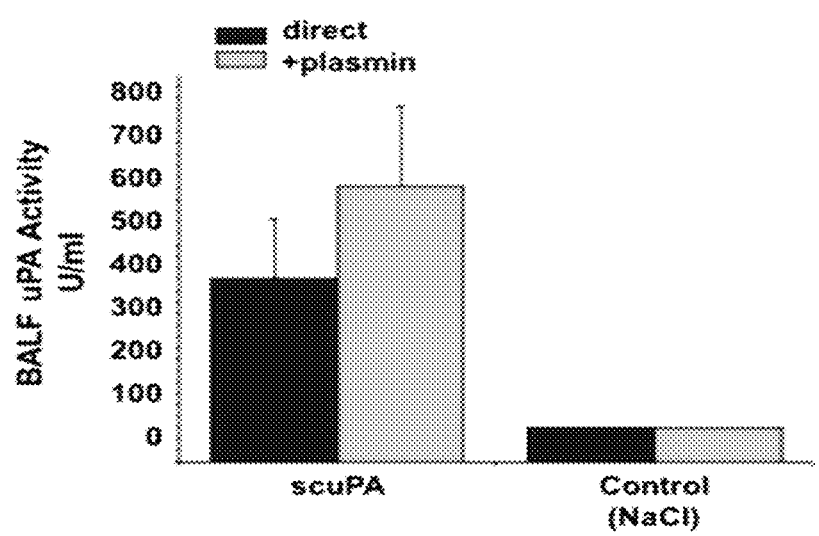
FIG. 1 is a graph showing that intratracheal delivery of recombinant scuPA in mice with bleomycin-induced ALI increases BAL uPA activity.

Example 1—Intratracheal Delivery of Recombinant scuPA in Mice with Bleomycin-Induced ALI Increases BAL uPA Activity ALI was induced in C57/B6 mice with 2.5 U/kg bleomycin at day 0 (n=10 animals/group). Mice were treated daily with 25,000 U; 167 µg/mouse of recombinant human scuPA via a microsprayer (100 µl). At day 7, BAL was obtained 4 hours after the last microsprayer administration of scuPA. uPA activity was measured using the amidolytic substrate S-2444 (directly+after incubation with 1 mU/ml plasmin for 5 hours). The results are shown in FIG. 1. The increment of uPA activity after plasmin treatment suggested that some of the nebulized scuPA remained intact within the alveolar lining fluids and remained available for activation by plasmin in vivo. No pulmonary or systemic bleeding occurred. These data confirm those of a previous report showing that nebulized scuPA increases lavage fibrinolytic activity in trauma-induced AL and is well-tolerated (Munster et al., 2002). The findings also show that durable fibrinolytic activity of scuPA (a substantive increase 4 hours after aerosolization) was generated in the lungs in ALI.

Figure 2:
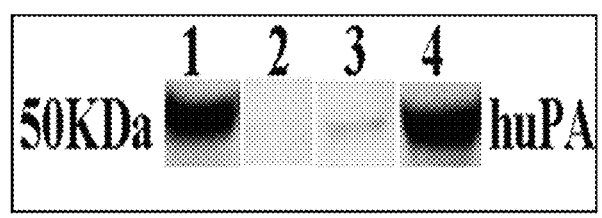
FIG. 2 shows that treatment of a sheep with nebulized scuPA provided detectable uPA activity associated with human uPA antigen after scuPA treatment (Lane 3). uPA antigen and activity were likewise found in lung homogenates (Lane 4) from the scuPA-treated animal. Lane 1: uPA standard and Lane 2: baseline uPA activity.

Example 2—Nebulized scuPA Lyses Airway Casts and is Detectable in BAL of Sheep with ISALI A sheep was treated with nebulized scuPA (2 mg/treatment begun 4 hours after induction of ISALI and continued every 4 hours×48 hours. Airway cast burden (obstruction score 12) fell into the range of sheep treated with nebulized tPA at 4 mg q 4 hours (vs. 20.7 in vehicle treated sheep with ISALI) (Enkhbaatar et al., 2004b). As shown in FIG. 2, BAL (bronchoalveolar lavage) of sheep had no detectable baseline uPA activity by fluorimetric analysis (Lane 2) but had detectable uPA activity associated with human uPA antigen after scuPA treatment (Lane 3) and uPA antigen and activity were likewise found in lung homogenates (Lane 4) from the scuPA-treated animal. Lane 1: uPA standard.

Example 3—Nebulized scuPA Lyses Airway Casts and is Detectable in BAL of Sheep with ISALI Studies were also conducted on scuPA solutions containing 1 mg/mL of scuPA dissolved in either physiological buffered saline or normal saline, and then nebulized using two types of vibrating mesh nebulizers, the EZ Breathe Atomizer and the AeroNeb Pro nebulizer. scuPA readily dissolved in both liquid carriers. It was confirmed that the activity of scuPA before and after nebulization was not affected by the nebulizing conditions (e.g., solution formation, shear and temperature from the nebulizing process in the nebulizer). Also, it was confirmed that the median geometric particle size for the scuPA solutions was 3-4 microns with a narrow and acceptable size distribution. The materials, methods and results are provided below and a schematic of the procedure is provided in FIG. 3.

Phosphate Buffered Saline and Sterile Saline Preparation:

The phosphate buffered saline (DPBS, Lot 14190-250, Gibco) was purchased from Biostore at UT-Austin. The compositions of the PBS were as shown in Table 1.

TABLE 1

| Components | Molecular Weight | Concentration (mg/L) | mM |
|---|---|---|---|
| Inorganic Salts | | | |
| Potassium Chloride (KCl) | 75 | 200 | 2.67 |
| Potassium Phosphate monobasic ($KH_2PO_4$) | 136 | 200 | 1.47 |
| Sodium Chloride (NaCl) | 58 | 8,000 | 137.93 |
| Sodium Phosphate dibasic ($Na_2HPO_4$—$7H_2O$) | 268 | 2,160 | 8.06 |

The pH of the PBS was 7.3±0.1. The sterile saline was purchased from B.Braun Medical Inc (Lot J1H573). Both preparations were stored at ambient room temperature, and excessive heat was avoided.

Device Introductions:

The EZ Breathe Atomizer nebulizer and AeroNeb pro nebulizer were used for testing. The Aeroneb® Professional Nebulizer System (vibrating mesh, Aerogen, Galway) was a portable medical device for multiple patient use. The Aeroneb® is intended to aerosolize physician-prescribed medications for inhalation that are approved for use with a general purpose nebulizer. The EZ Breathe Atomizer (vibrating mesh, Nephron Pharmaceuticals Corporation, USA) is a device that is intended to spray liquid medication in aerosol form into the air that a person will breathe. These devices can be used by patients with and without mechanical ventilation, or other positive pressure breathing assistance.

Scu-PA Solutions Preparation:

Eight vials each containing 3.5 mg/mL of scu-PA were obtained and stored at −80° C. In order to make two kinds of scu-PA solutions, the solutions were prepared in the following way:

A. scu-PA vials were held at room temperature (20° C.-25° C.) until they melted into solution. Two mL of the solution was transferred from the vial to a new 10 mL vial using a 6 mL syringe.

B. Using a 6 mL syringe with attached 21-gauge needle, 3 mL of sterile phosphate buffered saline (or sterile saline) was injected into one vial. The contents were manually agitated until all scu-PA solution was uniform. This solution was then diluted with sterile phosphate buffered saline (or sterile saline) to a final concentration of 1 mg/mL.

Geometric Particle-Size Distribution (PSD) Testing:

Both nebulizers were loaded with the two kinds of 5 mL scu-PA at a concentration of 1 mg/mL as samples and pure saline and pure PBS as blank controls, separately (8 samples in total). The geometric particle-size distribution (PSD) was determined using a Malvern Spraytec. A standard nebulization procedure was performed 5 times; each test lasted for 5 seconds. All determinations were carried out at ambient room temperature, barometric pressure, and humidity.

Samples Collected from Nebulizer for Further Study:

After 10 seconds, the nebulized procedure was started, and run until the aerosol generation was stable, after which 500 µL samples of the nebulized output scu-PA (4 samples in total) were collected and then frozen in the −80° C. refrigerator. Six samples were prepared as shown in Table 2.

TABLE 2

| | With sterile phosphate buffered saline | With sterile saline |
|---|---|---|
| Before nebulizing | 1(1) | 1(2) |
| After nebulizing | | |
| EZ Breathe Atomizer nebulizer | 1(3) | 1(5) |
| AeroNeb pro nebulizer | 1(4) | 1(6) |
| Total: 6 | | |

Results:

Table 3 denotes geometric particle-size distribution (PSD) information (n=5) of the samples and FIG. 4 shows the activity of each sample following nebulization.

TABLE 3

| Nebulizer name | Sample | Solvent | X(50%) µm | X(10%) µm | X(90%) µm |
|---|---|---|---|---|---|
| Aeroneb Pro | PBS | PBS | 3.14 | 0.87 | 7.74 |
| | Saline | Saline | 3.25 | 0.92 | 8.66 |
| | scu-PA | PBS | 3.83 | 0.96 | 11.40 |
| | scu-PA | Saline | 3.60 | 0.91 | 11.48 |
| EZ Breathe | PBS | PBS | 5.29 | 1.13 | 11.54 |
| Atomizer | Saline | Saline | 4.91 | 1.04 | 9.53 |
| | scu-PA | PBS | 4.79 | 1.16 | 11.17 |
| | scu-PA | Saline | 4.80 | 1.28 | 11.24 |

Based on these results, scuPA solutions are optimized for nebulization focusing on identifying the best nebulizer. Other parameters that are studied for nebulizer administration include confirming the effect of processing parameters (e.g., optimum solution composition for scuPA activity, aerodynamic properties including fine particle fraction, mass median aerodynamic diameter, and total emitted dose, temperature effects on scuPA activity during nebulization (e.g., using different nebulizer mechanism types), and the effects of shear (e.g., atomization pressure, ultrasonic vibrations, mesh size) of the liquid on scuPA activity.

Example 4—Suspension of tPA in PFCs is Stable and Preserves tPA Activity

FIG. 5 shows that suspension of tPA in PFCs is stable and that tPA activity is preserved. For these studies, the tPA/PFC suspensions (18 mL of the tPA-PFC suspension made at 0.22 mg/mL) were injected through the endotracheal tube (7 mm adult endotracheal tube) during the 50 minute hold time at 37° C. using a 10 mL syringe and 21 gauge needle. It was noted that the tPA was adequately wetted and deagglomerated in the PFCs. Other parameters that are studied for tPA administration include confirming the effect of processing parameters (e.g., particle size reduction of the tPA, viscosity of the PFC and resulting tPA-PFC suspension, solids content of the tPA-PFC suspension and its effect on administration during bronchoscopy on the tPA activity). The same approach is then used to analyze the formulations of the scuPA-PFC interventions.

The PFC and fibrinolysins additively foster airway debris removal as well as clearance of alveolar fibrin and improved outcome. Specifically, the PFC effectively delivers the fibrinolysins which promote 1) dissolution and dislodgement of the airway casts; and 2) removal of airway and alveolar debris while supporting respiratory gas exchange. Mechanistically, the PFC effectively recruits lung volume. Given the low surface tension of the PFC liquid, the PFC distributes the fibrinolysin throughout the lung, potentially between casts and airway wall, thus breaking down the casts as they are being formed while slowing formation of new casts. As the PFC volatizes from the lung, the fibrinolysin remains to further act to dissolve airway casts and alveolar fibrin. Upon redosing with PFC suspensions, the PFC volumes not only deposit additional drug but dislodge the casts and alveolar debris. Because the PFC is incompressible, it stents open damaged small airways and thereby aids recruitment. Contact with PFCs may also protect the underlying epithelium through attenuation of coagulation, which is initiated by tissue factor in the small airways and alveoli in virtually all forms of ALI. With in-line suctioning, the lower density debris float in the relatively more dense PFC, facilitating removal of airway fibrin cast fragments and debris.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Committee on injury and poison prevention (2000) *Pediatrics* 105:1355-1357
Enkhbaatar & Traber (2004) *Clin. Sci.* (Lond). 107:137-143
Enkhbaatar et al. (2004) *Shock.* 22:70-75
Enkhbaatar et al. (2008). *Clin. Sci.* (Lond). 114:321-329
Enkhbaatar, Herndon, and Traber (2008) *J Burn Care Res.* 30:159-162
O'Donnell (2012). *J. Pharm. Pract.* 25:22-29
Munster et al. (2002) *Blood Coagul. Fibrinolysis* 13:591-601
Phua et al. (2009) *Am J Respir Crit Care Med.* 179:220-227
Tuinman et al. (2012). *Crit Care* 16:R70
Waldrep and Dhand, (2008) *Current Drug Delivery,* 5(2): 114-119
U.S. Patent Publn. 20090134235

What is claimed is:

1. A method for treating a subject having a lung infection or lung injury, comprising administering to the lungs of the subject an amount of a composition comprising a plasminogen activator and a perfluorocarbon that is effective to treat the lung infection or lung injury.

2. The method of claim 1, wherein the subject has chemical-induced lung injury.

3. The method of claim 2, wherein the subject has plastic bronchitis, acute respiratory distress syndrome (ARDS) or inhalational smoke induced acute lung injury (ISALI).

4. The method of claim 1, wherein the subject has a lung infection.

5. The method of claim 1, further comprising delivering the composition to the lungs of the subject as a nebulized composition.

6. The method of claim 1, wherein the plasminogen activator is a single chain urokinase plasminogen activator (scuPA) or a tissue plasminogen activator (tPA).

7. The method of claim 6, wherein the plasminogen activator is a scuPA.

8. The method of claim 1, wherein the perfluorocarbon comprises a cycloalkyl group.

9. The method of claim 1, wherein the perfluorocarbon is selected from perfluorodecalin and perfluoro-octylbromide.

10. The method of claim 1, wherein the perfluorocarbon comprises perfluorodecalin.

11. A method of treating inhalational smoke induced acute lung injury (ISALI) in a subject comprising administering to the lungs of the subject a therapeutically effective amount of a composition comprising a plasminogen activator and a perfluorocarbon.

12. The method of claim 11, wherein the plasminogen activator is a single chain urokinase plasminogen activator (scuPA) or a tissue plasminogen activator (tPA).

13. The method of claim 11, wherein the plasminogen activator is a scuPA.

14. The method of claim 11, wherein the perfluorocarbon is selected from perfluorodecalin and perfluoro-octylbromide.

15. The method of claim 14, wherein the perfluorocarbon comprises perfluorodecalin.

* * * * *